(12) United States Patent
Sharifi-Mehr et al.

(10) Patent No.: US 10,952,776 B2
(45) Date of Patent: *Mar. 23, 2021

(54) GROWING RODS AND METHODS OF USE (71) Applicant: Stryker European Operations Holdings LLC, Kalamazoo, MI (US)

(72) Inventors: Amir Ali Sharifi-Mehr, Bloomingdale, NJ (US); Oliver Buchert, Franklin Lakes, NJ (US)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 52 days.

This patent is subject to a terminal disclaimer.

(21) Appl. No.: 16/133,069

(22) Filed: Sep. 17, 2018

(65) Prior Publication Data

US 2019/0083144 A1 Mar. 21, 2019

Related U.S. Application Data (63) Continuation of application No. 14/993,555, filed on Jan. 12, 2016, now Pat. No. 10,092,328.

(Continued)

(51) Int. Cl.
*A61B 17/70* (2006.01)
*A61B 17/00* (2006.01)

(52) U.S. Cl.
CPC ...... *A61B 17/7011* (2013.01); *A61B 17/7002* (2013.01); *A61B 17/7004* (2013.01); *A61B 17/7014* (2013.01); *A61B 17/7016* (2013.01); *A61B 17/7017* (2013.01); *A61B 2017/00221* (2013.01); *A61B 2017/00539* (2013.01)

(58) Field of Classification Search
CPC .......... A61B 17/7011; A61B 17/7002; A61B 17/7014; A61B 17/7017; A61B 17/7004; A61B 2017/00539
See application file for complete search history.

(56) References Cited

U.S. PATENT DOCUMENTS 3,976,060 A 8/1976 Hildebrandt et al.
4,078,559 A 3/1978 Nissinen
(Continued)

FOREIGN PATENT DOCUMENTS

EP 3047810 A1 7/2016
JP H9504185 A 4/1997
(Continued)

OTHER PUBLICATIONS

Australian Search Report for Application No. AU2017216532 dated Sep. 10, 2019, 1 page.
(Continued)

*Primary Examiner* — Eduardo C Robert
*Assistant Examiner* — Tara Rose E Carter
(74) *Attorney, Agent, or Firm* — Lerner, David, Littenberg, Krumholz & Mentlik, LLP (57) ABSTRACT Hydraulically expandable spinal rods and methods of use thereof are disclosed. The spinal rod may include a piston rod, a static rod, and a hydraulic pressure chamber for accepting hydraulic fluid and causing the piston rod to move in an expansion direction relative to the static rod. Upon connection of the piston and static rods to a patient's spinal column, the hydraulic spinal rod may be expanded to aid in correction of an underlying spinal deformity.

14 Claims, 10 Drawing Sheets

Related U.S. Application Data (60) Provisional application No. 62/102,778, filed on Jan. 13, 2015.

(56) References Cited

U.S. PATENT DOCUMENTS

| | | |
|---|---|---|
| 4,289,123 A | 9/1981 | Dunn |
| 4,445,513 A | 5/1984 | Ulrich et al. |
| 4,611,580 A | 9/1986 | Wu |
| 4,611,582 A | 9/1986 | Duff |
| 4,658,809 A | 4/1987 | Ulrich et al. |
| 4,827,918 A | 5/1989 | Olerud |
| 4,931,055 A | 6/1990 | Bumpus et al. |
| 4,957,495 A | 9/1990 | Kluger |
| 5,034,011 A | 7/1991 | Howland |
| 5,129,388 A | 7/1992 | Vignaud et al. |
| 5,330,472 A | 7/1994 | Metz-Stavenhagen |
| 5,350,379 A | 9/1994 | Spievack |
| 5,505,733 A | 4/1996 | Justin et al. |
| 5,575,790 A | 11/1996 | Chen et al. |
| 5,626,579 A | 5/1997 | Muschler et al. |
| 5,704,939 A | 1/1998 | Justin |
| 5,720,746 A | 2/1998 | Soubeiran |
| 5,762,599 A | 6/1998 | Sohn |
| 5,810,815 A | 9/1998 | Morales |
| 6,245,075 B1 | 6/2001 | Betz et al. |
| 6,416,516 B1 | 7/2002 | Stauch et al. |
| 6,417,750 B1 | 7/2002 | Sohn |
| 6,500,177 B1 | 12/2002 | Martinelli et al. |
| 6,783,530 B1 | 8/2004 | Levy |
| 6,849,076 B2 | 2/2005 | Blunn et al. |
| 6,918,910 B2 | 7/2005 | Smith et al. |
| 7,011,658 B2 | 3/2006 | Young |
| 7,063,706 B2 | 6/2006 | Wittenstein |
| 7,135,022 B2 | 11/2006 | Kosashvili et al. |
| 7,481,841 B2 | 1/2009 | Hazebrouck et al. |
| 7,655,026 B2 | 2/2010 | Justis et al. |
| 7,666,184 B2 | 2/2010 | Stauch |
| 7,666,207 B2 | 2/2010 | Schlapfer et al. |
| 7,699,879 B2 | 4/2010 | Sherman et al. |
| 7,753,915 B1 | 7/2010 | Eksler et al. |
| 7,763,053 B2 | 7/2010 | Gordon |
| 7,776,075 B2 | 8/2010 | Bruneau et al. |
| 7,776,091 B2 | 8/2010 | Mastrorio et al. |
| 7,780,705 B2 | 8/2010 | Shaolian et al. |
| 7,806,913 B2 | 10/2010 | Fanger et al. |
| 7,842,036 B2 | 11/2010 | Phillips |
| 7,927,357 B2 | 4/2011 | Sadler et al. |
| 7,938,848 B2 | 5/2011 | Sweeney |
| 7,942,908 B2 | 5/2011 | Sacher et al. |
| 7,955,357 B2 | 6/2011 | Kiester |
| 8,016,837 B2 | 9/2011 | Giger et al. |
| 8,016,860 B2 | 9/2011 | Carl et al. |
| 8,043,290 B2 | 10/2011 | Harrison et al. |
| 8,057,472 B2 | 11/2011 | Walker et al. |
| 8,092,499 B1 | 1/2012 | Roth |
| 8,100,943 B2 | 1/2012 | Malandain et al. |
| 8,114,133 B2 | 2/2012 | Logan |
| 8,142,454 B2 | 3/2012 | Harrison et al. |
| 8,177,812 B2 | 5/2012 | Sankaran |
| 8,202,301 B2 | 6/2012 | Prevost et al. |
| 8,211,149 B2 | 7/2012 | Justis |
| 8,252,063 B2 | 8/2012 | Stauch |
| 8,277,489 B2 * | 10/2012 | Saidha ............... A61B 17/7049 606/251 |
| 8,287,541 B2 | 10/2012 | Nelson et al. |
| 8,292,927 B2 | 10/2012 | Rouleau et al. |
| 8,298,240 B2 | 10/2012 | Giger et al. |
| 8,343,192 B2 | 1/2013 | Kiester |
| 8,372,121 B2 | 2/2013 | Capote et al. |
| 8,439,915 B2 | 5/2013 | Harrison et al. |
| 8,475,499 B2 | 7/2013 | Cournoyer et al. |
| 8,486,112 B2 | 7/2013 | Fanger et al. |
| 8,568,457 B2 | 10/2013 | Hunziker |
| 8,585,740 B1 | 11/2013 | Ross et al. |
| 8,623,036 B2 | 1/2014 | Harrison et al. |
| 8,663,285 B2 | 3/2014 | Dall et al. |
| 8,721,643 B2 | 5/2014 | Morgan et al. |
| 8,764,751 B2 | 7/2014 | Orbay et al. |
| 8,777,947 B2 | 7/2014 | Zahrly et al. |
| 8,814,909 B2 | 8/2014 | Fanger et al. |
| 8,852,233 B2 | 10/2014 | Burke |
| 8,894,663 B2 | 11/2014 | Giger et al. |
| 8,894,688 B2 | 11/2014 | Suh |
| 8,915,915 B2 | 12/2014 | Harrison et al. |
| 8,915,917 B2 | 12/2014 | Doherty et al. |
| 8,956,392 B2 | 2/2015 | Khatchadourian et al. |
| 8,961,567 B2 | 2/2015 | Hunziker |
| 8,974,500 B2 | 3/2015 | Khatchadourian et al. |
| 8,992,527 B2 | 3/2015 | Guichet |
| 9,060,810 B2 | 6/2015 | Kercher et al. |
| 9,144,438 B2 | 9/2015 | Suh |
| 2003/0220643 A1 | 11/2003 | Ferree |
| 2004/0023623 A1 | 2/2004 | Stauch et al. |
| 2005/0277921 A1* | 12/2005 | Eisermann ............ A61F 2/4405 623/17.16 |
| 2006/0106381 A1 | 5/2006 | Ferree et al. |
| 2006/0293683 A1 | 12/2006 | Stauch |
| 2007/0010814 A1 | 1/2007 | Stauch |
| 2007/0050036 A1 | 3/2007 | Felt et al. |
| 2007/0255237 A1 | 11/2007 | Lobl et al. |
| 2008/0027436 A1* | 1/2008 | Cournoyer ......... A61B 17/7079 606/250 |
| 2008/0045951 A1 | 2/2008 | Fanger et al. |
| 2008/0177319 A1 | 7/2008 | Schwab |
| 2008/0208260 A1 | 8/2008 | Truckai et al. |
| 2009/0030462 A1 | 1/2009 | Buttermann |
| 2009/0112207 A1 | 4/2009 | Walker et al. |
| 2009/0118774 A1 | 5/2009 | Miller, III |
| 2009/0204156 A1 | 8/2009 | McClintock et al. |
| 2009/0234388 A1 | 9/2009 | Patterson et al. |
| 2009/0275984 A1 | 11/2009 | Kim et al. |
| 2009/0306717 A1* | 12/2009 | Kercher ............ A61B 17/7011 606/258 |
| 2010/0106192 A1 | 4/2010 | Barry |
| 2010/0137913 A1 | 6/2010 | Khatchadourian et al. |
| 2010/0137914 A1 | 6/2010 | Ritland |
| 2010/0152776 A1 | 6/2010 | Keyer et al. |
| 2010/0211105 A1 | 8/2010 | Moumene et al. |
| 2010/0318130 A1 | 12/2010 | Parlato et al. |
| 2011/0184463 A1 | 7/2011 | Schwend |
| 2011/0196371 A1 | 8/2011 | Forsell |
| 2011/0196435 A1* | 8/2011 | Forsell ............... A61B 17/7062 606/86 R |
| 2011/0238126 A1 | 9/2011 | Soubeiran |
| 2012/0035661 A1 | 2/2012 | Pool et al. |
| 2012/0053633 A1 | 3/2012 | Stauch |
| 2012/0130428 A1 | 5/2012 | Hunziker |
| 2012/0130432 A1 | 5/2012 | Ferree et al. |
| 2012/0271353 A1 | 10/2012 | Barry |
| 2012/0296234 A1 | 11/2012 | Wilhelm et al. |
| 2013/0072932 A1 | 3/2013 | Stauch |
| 2013/0096615 A1 | 4/2013 | Kiester |
| 2013/0150889 A1 | 6/2013 | Fening et al. |
| 2013/0282064 A1* | 10/2013 | Arnin ................ A61B 17/7014 606/258 |
| 2013/0338713 A1 | 12/2013 | Kawakami et al. |
| 2013/0338714 A1 | 12/2013 | Chang et al. |
| 2014/0074168 A1 | 3/2014 | Mundis et al. |
| 2014/0135769 A1 | 5/2014 | Ziran |
| 2014/0142631 A1 | 5/2014 | Hunziker |
| 2014/0222074 A1 | 8/2014 | Rathbun et al. |
| 2014/0277147 A1 | 9/2014 | Alexander et al. |
| 2014/0296918 A1 | 10/2014 | Fening et al. |
| 2014/0324047 A1 | 10/2014 | Zahrly et al. |
| 2015/0051647 A1 | 2/2015 | Suh |
| 2015/0127002 A1 | 5/2015 | Doherty et al. |
| 2015/0134002 A1 | 5/2015 | Khatchadourian et al. |
| 2015/0150601 A1 | 6/2015 | Giger et al. |
| 2015/0157364 A1 | 6/2015 | Hunziker |
| 2016/0120580 A1 | 5/2016 | Johnston, Jr. et al. |

(56) References Cited

U.S. PATENT DOCUMENTS

2017/0095273 A1    4/2017  Lynch et al.
2018/0028234 A1    2/2018  Simpson et al.

FOREIGN PATENT DOCUMENTS

| JP | 2009535155 A  | 10/2009 |
| JP | 2011502003 A  | 1/2011  |
| JP | 2011072471 A  | 4/2011  |
| WO | 9009156 A1    | 8/1990  |
| WO | 9522292 A1    | 8/1995  |
| WO | 2007090021 A1 | 8/2007  |
| WO | 2007123920 A2 | 11/2007 |
| WO | 2010062718 A1 | 6/2010  |
| WO | 2011027126 A1 | 3/2011  |
| WO | 2011068851 A1 | 6/2011  |
| WO | 2011116773 A1 | 9/2011  |
| WO | 2012024335 A2 | 2/2012  |
| WO | 2012044371 A1 | 4/2012  |

OTHER PUBLICATIONS

Extended European Search Report for Application No. EP19171279.3 dated Sep. 3, 2019, pp. 1-4.
European Seach Report for Application No. EP16151087 dated Jun. 20, 2016.
Australian Search Report for Application No. 2017216532 dated Oct. 16, 2019, 1 page.
Extended European Search Report for EP Application No. 18176053.9, dated Oct. 2, 2018.

* cited by examiner

GROWING RODS AND METHODS OF USE

CROSS-REFERENCE TO RELATED APPLICATIONS

The present application is a continuation of U.S. patent application Ser. No. 14/993,555, filed Jan. 12, 2016, which claims the benefit of the filing date of U.S. Provisional Application No. 62/102,778, filed Jan. 13, 2015, the disclosure of which is hereby incorporated by reference herein.

BACKGROUND OF THE INVENTION

The present invention(s) relates to spinal rods capable of expansion for treating a variety of spinal maladies.

A scoliotic spine is one in which the spinal column is abnormally curved in one or more different directions, causing resultant adverse side effects for the person suffering from the deformity. Surgeons have attempted to correct this abnormal curvature, in some cases, with spinal rods implanted on the patient's spinal column. The spinal rods exert a force on the spinal column to correct and restore the natural curvature thereof. Pediatric scoliosis is a particular spinal deformity that is marred with a common issue—the patient is young and growing and, consequently, the patient's spinal column is growing as well. Thus, any effort to straighten the young patient's spinal column with, for example, a fixed-length rod is likely to encounter a problem. Namely, as the spine grows the fixed-length rod does not allow further thoracic growth in the patient. As a result, expandable spinal rods have developed to accommodate the growing spine in pediatric patients.

Examples of existing expandable spinal rods include magnetic growing spinal rods and mechanically distractible spinal rods. In the case of magnet growing spinal rods, some include a motor actuated by an external magnet to cause separate rod portions to distract and, consequently, lengthen the overall spinal rod. Mechanically distractible spinal rods typically have rod portions that are manually movable relative to each other via a distraction instrument. The rod portions are distracted during multiple different surgeries to cause lengthening of the overall spinal rod and correction of the underlying deformity. Magnetic growing rods suffer from a number of defects, however, namely distraction forces are limited by the strength of the motor used therewith. In addition, the overall rod is not susceptible to common medical imaging techniques (e.g., magnetic resonance imaging (MRI)) used during surgery. Mechanically-distractible rods also suffer downsides, for example multiple invasive surgical interventions are required after the initial, primary surgery to lengthen the rod (e.g., by use of a distractor instrument). The patient therefore suffers from the side effects of multiple invasive surgeries to correct the spinal deformity.

There is therefore a need for an improved spinal rod device usable to correct, for example, scoliosis of the spine.

BRIEF SUMMARY OF THE INVENTION

A first aspect of the invention includes a spinal rod. The rod comprises a first rod portion having an elongate rod section adapted for connection with a first fixation element implanted in a first vertebra, the first rod portion including an internal hollow cavity defined by an internal wall surface, and a second rod portion having an elongate rod section adapted for connection with a second fixation element implanted in a second vertebra, wherein the second rod portion is inserted within the internal cavity of the first rod portion and is axially movable relative to the first rod portion within the internal cavity in an expansion direction. The rod is sealingly engaged to the internal wall surface and thereby defines a hydraulic pressure chamber, the hydraulic pressure chamber being fluidly sealed off from the internal hollow cavity. Further, the spinal rod includes an injection port and a flow channel in fluid communication with the hydraulic pressure chamber, as well as a locking mechanism engageable with the second rod portion, the locking mechanism being effective to lock the second rod portion relative to the first rod portion, wherein the locking mechanism includes a release mechanism allowing for disengagement between the locking mechanism and the second rod portion to permit movement of the second rod portion in a contraction direction opposite the expansion direction.

In an embodiment of this first aspect, the elongate rod section of the first rod portion is fixed relative to its internal hollow cavity. In another example, the injection port and the locking mechanism are in close proximity to each other.

A second aspect of the invention includes a spinal rod. The rod comprises a first rod portion having an elongate rod section adapted for connection with a first fixation element implanted in a first vertebra, the first rod portion including an internal hollow cavity defined by an internal wall surface, and a second rod portion having an elongate rod section adapted for connection with a second fixation element implanted in a second vertebra, wherein the second rod portion is inserted within the internal cavity of the first rod portion and is axially movable relative to the first rod portion within the internal cavity in an expansion direction. The rod is sealingly engaged to the internal wall surface and thereby defines a hydraulic pressure chamber, the hydraulic pressure chamber being fluidly sealed off from the internal hollow cavity. Further, the spinal rod includes an injection port and a flow channel in fluid communication with the hydraulic pressure chamber, as well as a locking mechanism engageable with the second rod portion, the locking mechanism being effective to lock the second rod portion relative to the first rod portion, wherein the injection port and the locking mechanism are in close proximity to each other.

In an embodiment of this second aspect, the injection port and the locking mechanism are adjacent each other on a same side of the first rod portion. Further, the injection port and the locking mechanism may be spaced apart by anywhere from between about 5 mm to about 9 mm. In another embodiment, the locking mechanism is a set screw operable to bear on the second rod portion and lock it relative to the first rod portion, or it is a ratchet and pawl mechanism operable to lock the first rod portion relative to the second rod portion.

A third aspect of the invention includes a method of operating a spinal rod. The method comprises engaging an elongate rod section of a first rod portion of a spinal rod with a first fixation element implanted in a first vertebra of a spine, the first rod portion including an internal hollow cavity defined by an internal wall surface, and engaging an elongate rod section of a second rod portion of the spinal rod with a second fixation element implanted in a second vertebra of the spine, the second rod portion being inserted within the internal cavity of the first rod portion and sealingly engaging the internal wall surface to thereby define a hydraulic pressure chamber. The method also comprises introducing hydraulic fluid into the hydraulic pressure chamber through an injection port of the spinal rod so that the hydraulic fluid acts on the second rod portion and causes it to move in an expansion direction within the internal cavity.

Further, the second rod portion is locked relative to the first rod portion after the introducing step. Optionally, the hydraulic fluid is subsequently withdrawn out of the hydraulic pressure chamber.

In an embodiment of this third aspect, the small incision is anywhere from between about 4 mm to about 5 mm in length. In another example, the hydraulic pressure chamber is a remote distance from the injection port, and the method further comprises causing the hydraulic fluid to pass through the injection port, into a flow channel extending between the injection port and the hydraulic pressure chamber, and subsequently into the hydraulic pressure chamber, the flow channel extending substantially parallel to the internal cavity along at least a part of its length.

BRIEF DESCRIPTION OF THE DRAWINGS

A more complete appreciation of the subject matter of the present invention(s) and of the various advantages thereof can be realized by reference to the following detailed description in which reference is made to the accompanying drawings in which.

DETAILED DESCRIPTION

In describing the preferred embodiments of the invention(s), specific terminology will be used for the sake of clarity. However, the invention(s) is not intended to be limited to any specific terms used herein, and it is to be understood that each specific term includes all technical equivalents, which operate in a similar manner to accomplish a similar purpose.

Figures 1A, 1B:
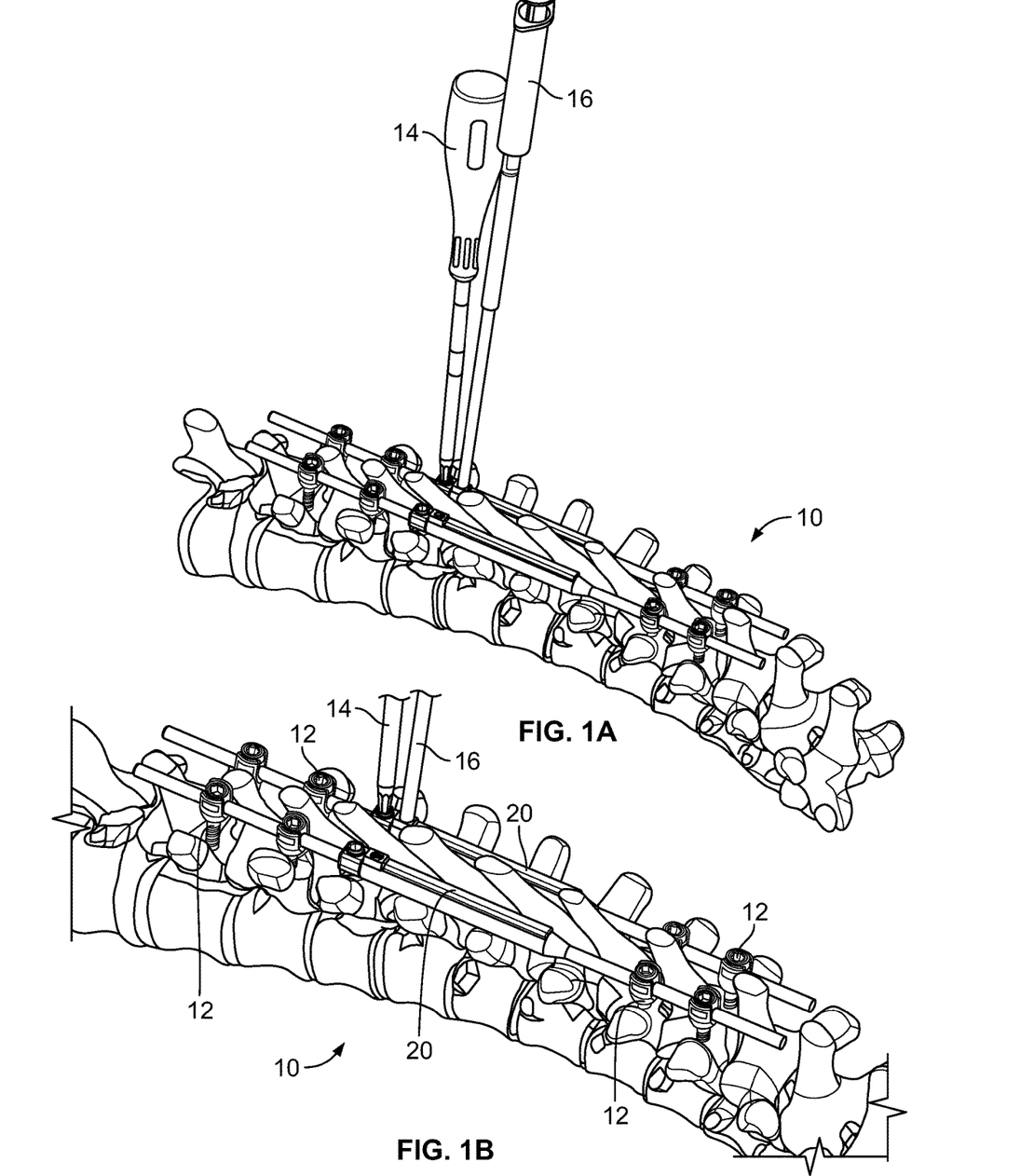
FIG. 1A is a perspective view of multiple spinal rods according to an embodiment of the present invention, which are implanted side-by-side on a spinal column of a patient.
FIG. 1B is a close-up perspective view of FIG. 1A.

Referring to FIGS. 1A-B, a spinal column 10 is shown with multiple hydraulic rods 20 implanted thereon. As illustrated in FIG. 1B, each rod 20 is connected at both ends to one or more pedicle screw devices 12 implanted in respective vertebra of spinal column 10. Pedicle screw devices 12 may be any screw construct commonly known in the art including, for example, pedicle screw constructs that utilize a head with an open channel (referred to as a tulip) for accommodating a portion of a rod, and a threaded screw shank for insertion into a vertebra of spinal column 10. Of course, spinal hooks or other common suitable fixation devices may be used in place of pedicle screws 12, as would be recognized by one of skill in the art. In any case, each hydraulic spinal rod 20 may be attached to pedicle screws 12 and expanded at will. Rods 20 may use hydraulic technology to achieve expansion, as described in more detail below. Thus, rods 20 allow for expansion at selected intervals after initial implantation to accommodate changing surgical parameters (e.g., the growing spine of a pediatric patient suffering from scoliosis).

Figure 2A:
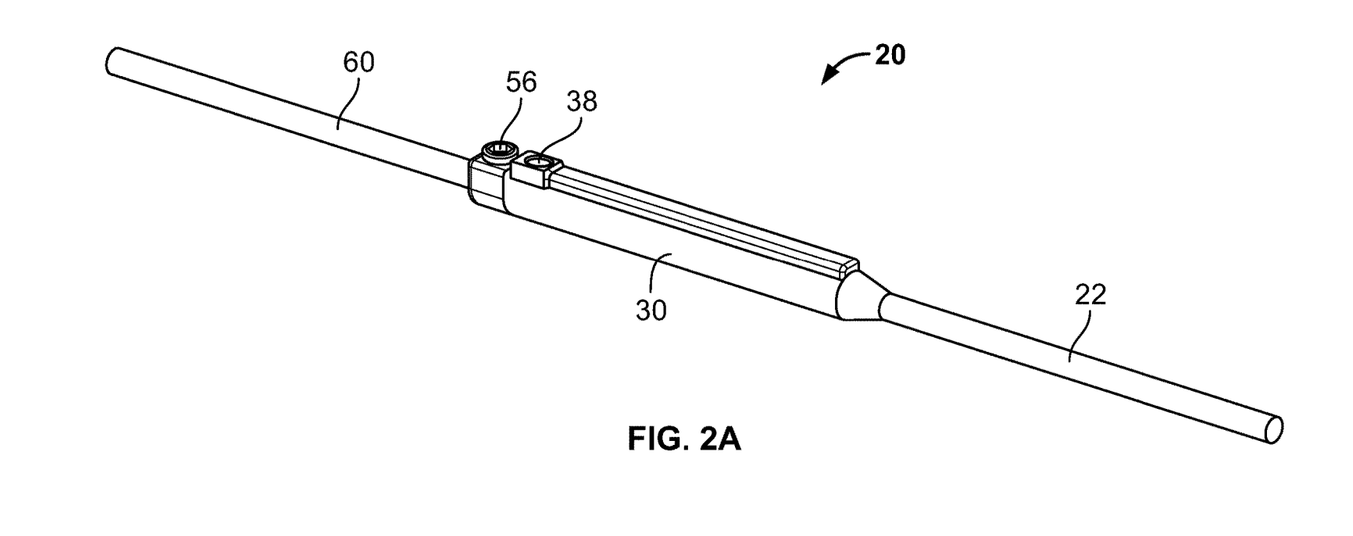
FIG. 2A is a perspective view of a first embodiment of a spinal rod according to the present invention.
Figure 2B:
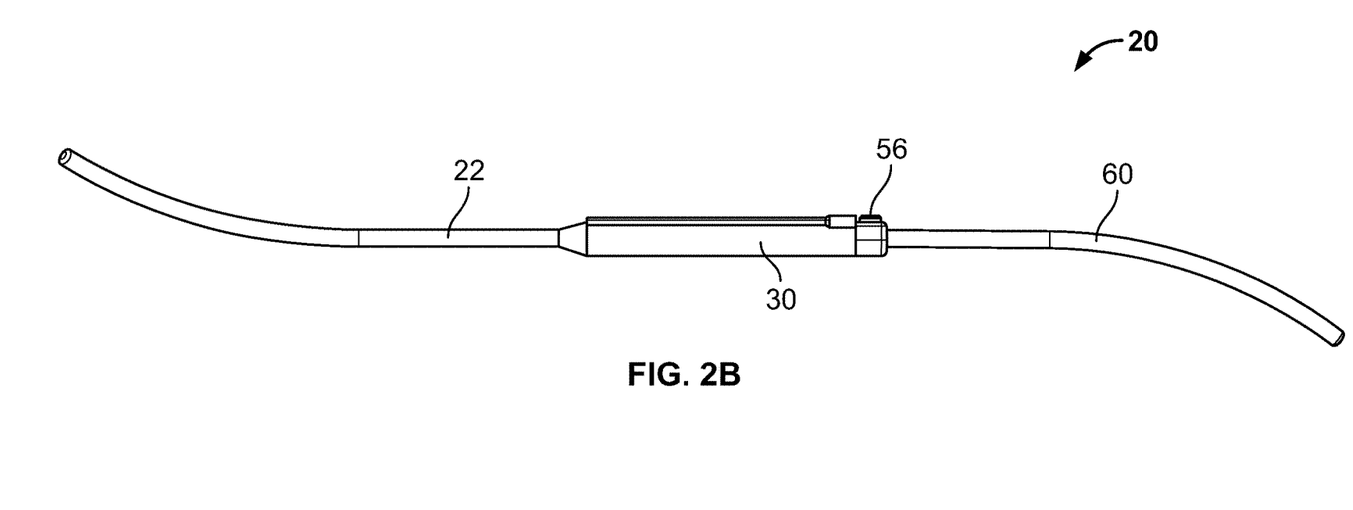
FIG. 2B is a side view of a second embodiment of a spinal rod according to the present invention.

As shown in FIGS. 2A-B, spinal rod 20 includes multiple rod portions, namely a static rod 22 and a piston rod 60. Both static and piston rods 22, 60 may be straight (FIG. 2A), pre-bent (FIG. 2B) to accommodate the curvature of the spine 10 of a particular patient, or may be designed to be bent during surgery (transition from FIG. 2A to 2B) to accommodate a particular amount of spinal curvature. As shown in FIG. 2B, in one embodiment an end section of static rod 22 may be curved upwards (e.g., for fixation to the lumbar spine exhibiting a lordotic curvature) while an end section of piston rod 60 may be curved downwards (e.g., for fixation to the thoracic spine exhibiting a kyphotic curvature). Of course, static and piston rods 22, 60 may be bent in any direction in any combination at the discretion of the surgeon, or at the time of manufacturing.

Figure 3:
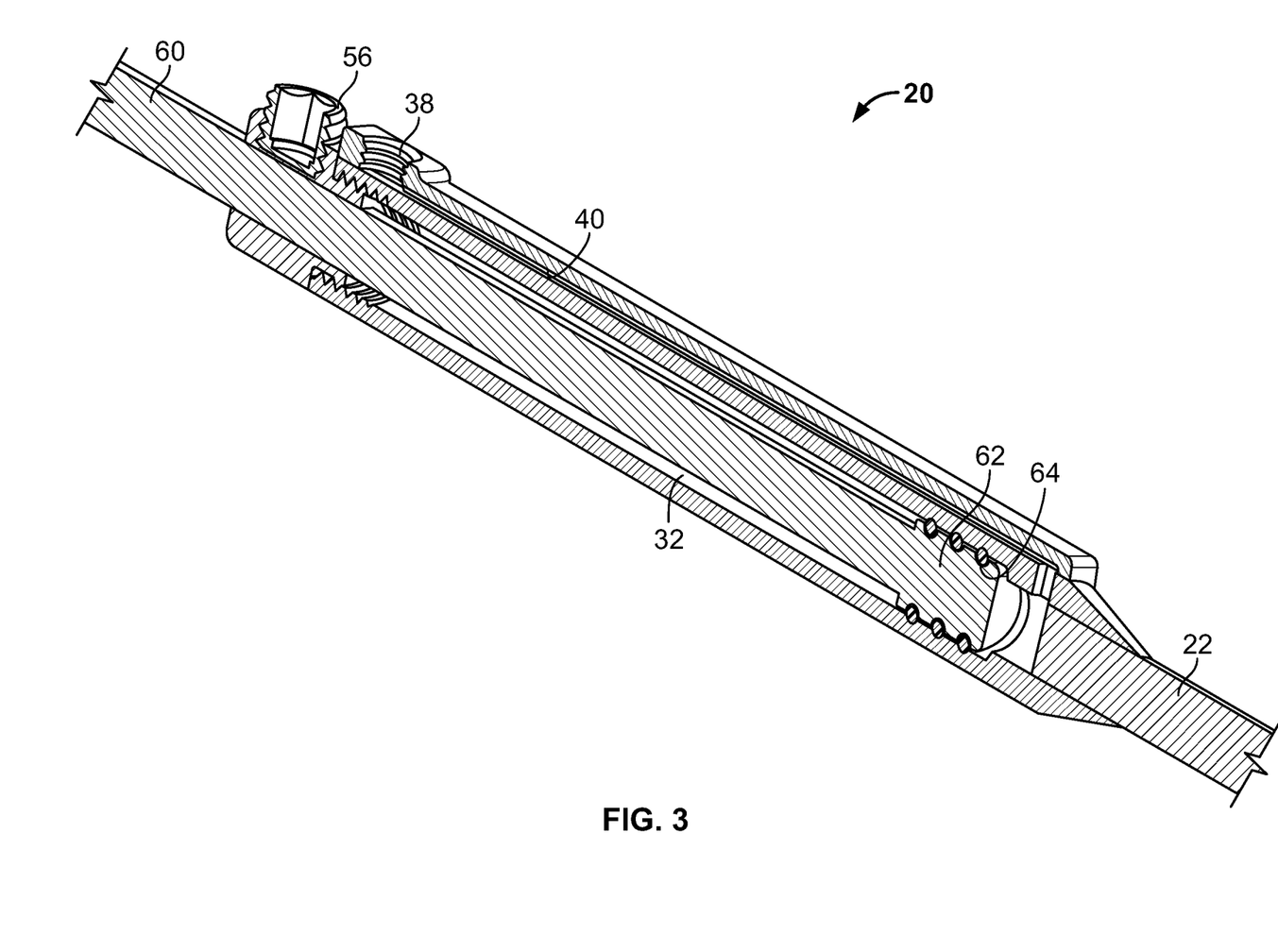
FIG. 3 is a cross-sectional view of the hydraulic expansion mechanism of the spinal rods shown in FIGS. 2A-B.
Figure 4A:
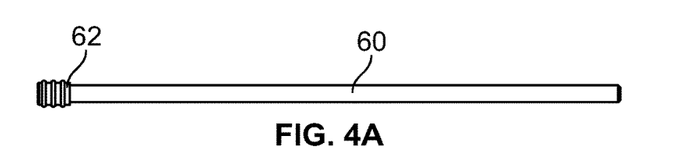
FIGS. 4A-D are side, top, cross-sectional, and perspective views of a piston rod forming part of the spinal rod of FIGS. 2A-B.
Figure 4B:
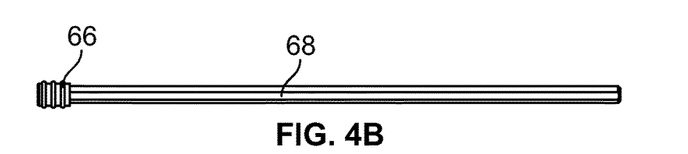
Figure 4C:
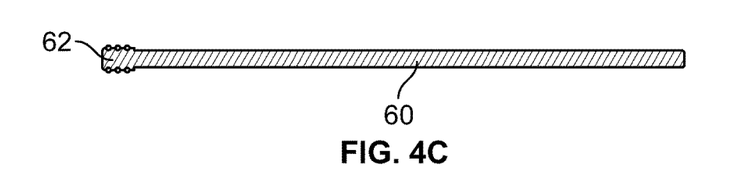
Figure 4D:
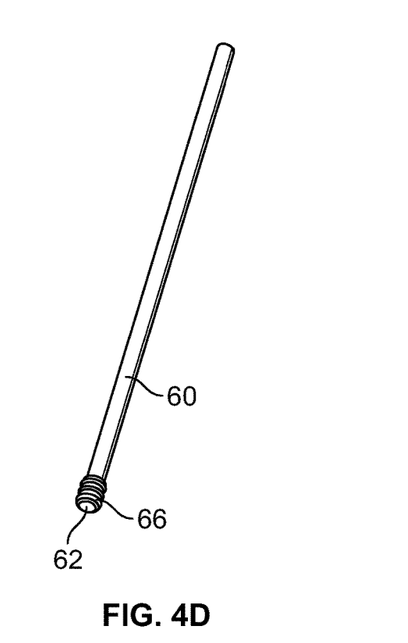
Figure 5A:
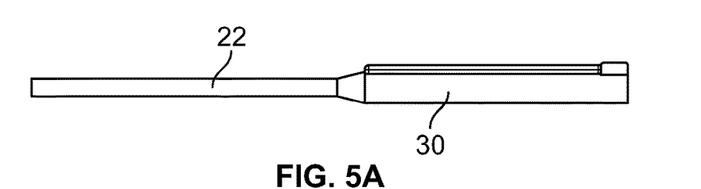
FIGS. 5A-D are side, top, cross-sectional, and perspective views of a static rod and hydraulic cylinder forming part of the spinal rod of FIGS. 2A-B.
Figure 5B:
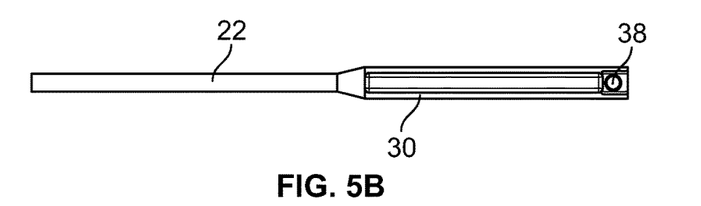
Figure 5C:
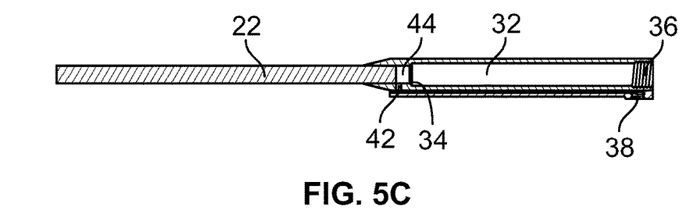
Figure 5D:
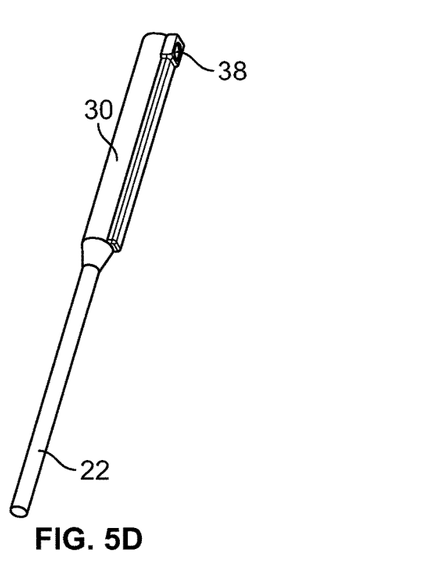
Figure 6A:
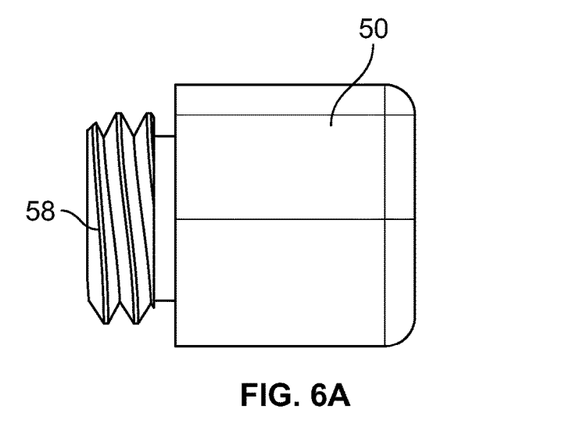
FIGS. 6A-D are side, top, cross-sectional, and perspective views of a capture nut forming part of the spinal rod of FIGS. 2A-B.
Figure 6B:
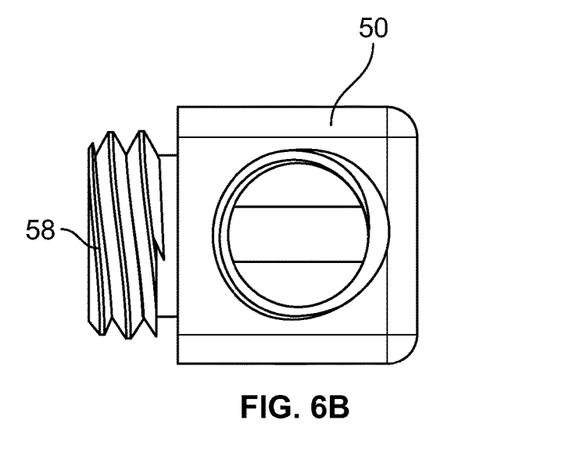
Figure 6C:
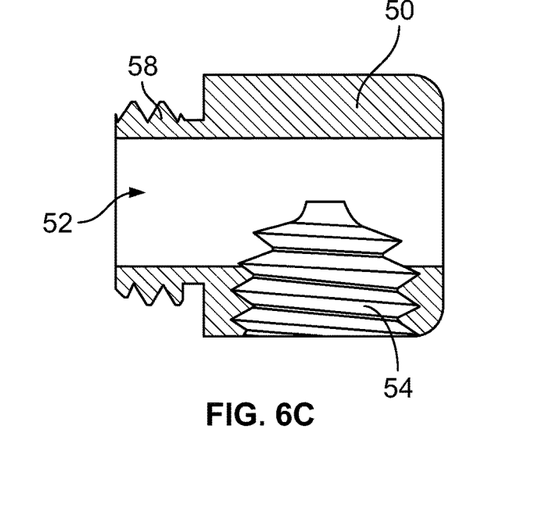
Figure 6D:
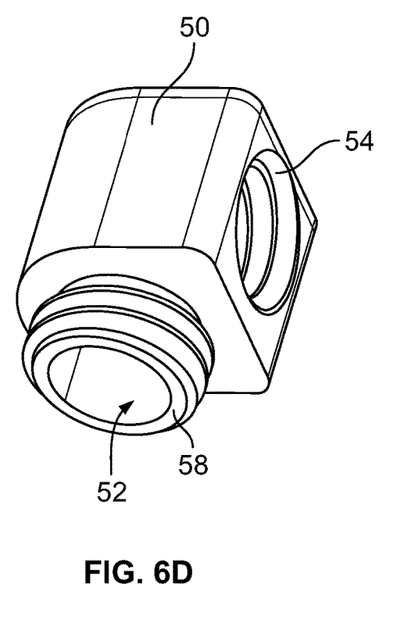

FIG. 3 depicts a cross-sectional assembly view of the hydraulic expansion mechanism of rod 20, the components of which are shown in more detail in FIGS. 4A-7B. Referring to FIGS. 4A-D, piston rod 60 is shown in various views. Piston rod 60 has an elongate rod section adapted for connection with pedicle screws 12, and an end portion 62 having a diameter/dimension larger than a diameter/dimension of the remainder of piston rod 60. In one embodiment, end portion 62 includes one or more circumferential recesses 64, shown best in FIGS. 3 and 7D, for accommodating one or more seals 66 (e.g., O-rings). As shown in FIG. 4B, piston rod 60 may also be irregular or otherwise non-circular in shape. For instance, it may include a flat section 68 running along substantially an entire length (or only a portion) of its elongate section. The irregular shape of piston rod 60 may ensure that it remains in a rotatably-fixed position once incorporated into the rest of the assembly of hydraulic rod 20. Thus, piston rod 60 may be "keyed" in one embodiment.

Static rod 22 is shown in detail in FIGS. 5A-D. In one embodiment, static rod 22 includes an elongate rod section that is connected (in some cases integral or monolithic with) a hydraulic cylinder 30. As described above, the elongate section of static rod 22 can be bent in any number of directions, during surgery or at manufacturing, to accommodate a particular spinal curvature, or it may be straight. Hydraulic cylinder 30 includes an internal cavity 32 that is, in one example, cylindrical in shape. Internal cavity 32 is sized to receive end portion 62 of piston rod 60 to allow piston rod 60 to reciprocate and move axially within internal cavity 32 (e.g., for rod-elongation purposes). Movement of piston rod 60 within internal cavity 32 is limited by a step or stop 34 formed in internal cavity 32 adjacent the elongate rod section of static rod 22. In one embodiment, the diameter/dimension of an opening defined by step/stop 34 is smaller than the diameter/dimension of end portion 62 of piston rod 60 so that end portion 62 can contact step/stop 34 and prevent movement of piston rod 60 past step/stop 34. Beyond such limiting features (and others described with reference to capture nut 50 below), piston rod 60 is freely movable within internal cavity 32.

Hydraulic cylinder 30 also includes a flow injection port or opening 38 (FIGS. 5B-D) for injection of hydraulic fluid into internal cavity 32. In one embodiment, injection port 38 is threaded. Injection port 38 leads into a flow channel 40 in hydraulic cylinder 30 that defines a passageway for allowing fluid (e.g., incompressible hydraulic fluid) to flow within flow channel 40. Flow channel 40 is shown best in FIGS. 3 and 7C-D. Flow channel 40 has an opening 42 at an end thereof, which leads into a hydraulic pressure chamber 44. Hydraulic pressure chamber 44 is cylindrical, in one embodiment, and it fluidly communicates with internal cavity 32 of hydraulic cylinder 30. In one case, hydraulic pressure chamber 44 forms part of internal cavity 32. Further, hydraulic pressure chamber 44 is sealed at one end via the elongate section of static rod 22 connected to hydraulic cylinder 30. Thus, fluid (e.g., incompressible hydraulic fluid) can travel through injection port 38, into flow channel 40, through opening 42, and finally into hydraulic pressure chamber 44 of hydraulic cylinder 30 during use. Although not shown, hydraulic rod 20 may also include a plug (optionally threaded) for insertion into injection port 38 when it is not in use. In addition, in an embodiment injection port 38 and flow channel 38 are welded onto hydraulic cylinder 30, although such structures may be integral or unitary in another embodiment.

FIGS. 6A-D show a capture nut 50, which includes a threaded projecting part 58, a channel 52, and a threaded opening 54 for receiving a set screw 56 (shown in FIGS. 7A-D). Channel 52 is sized and shaped to receive the elongate rod section of piston rod 60 so that piston rod 60 can reciprocate and move within capture nut 50. Likewise, threaded opening 54 is sized to receive set screw 56 to allow set screw 56 to be screwed into opening 54 and bear on piston rod 60 to secure it relative to capture nut 50 and static rod 22. In one embodiment, channel 52 is also irregularly shaped in the same manner as the elongate rod section of piston rod 60 (e.g., it may include a flat portion (not shown) similar to flat section 68) so that, when piston rod 60 is received in channel 52, it is not rotatably movable relative to capture nut 50. Thus, channel 52 of capture nut 50 may be "keyed" as well.

Figure 7A:
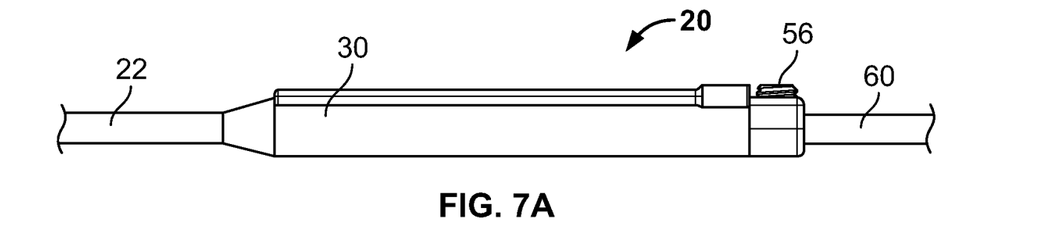
FIGS. 7A-C are side, top, and cross-sectional views of a section of the spinal rods of FIGS. 2A-B.
Figure 7B:
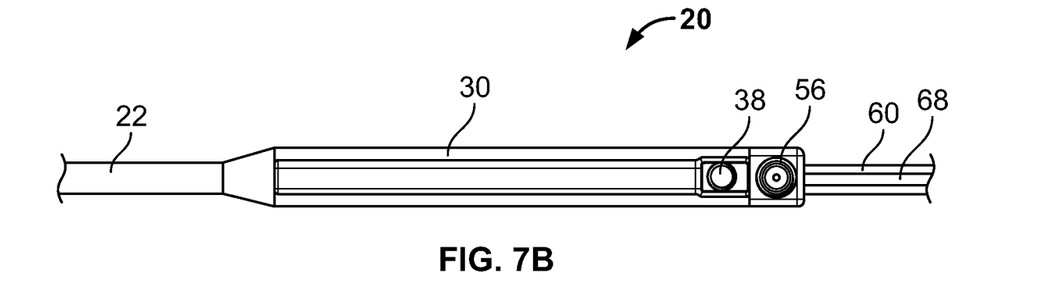
Figure 7C:
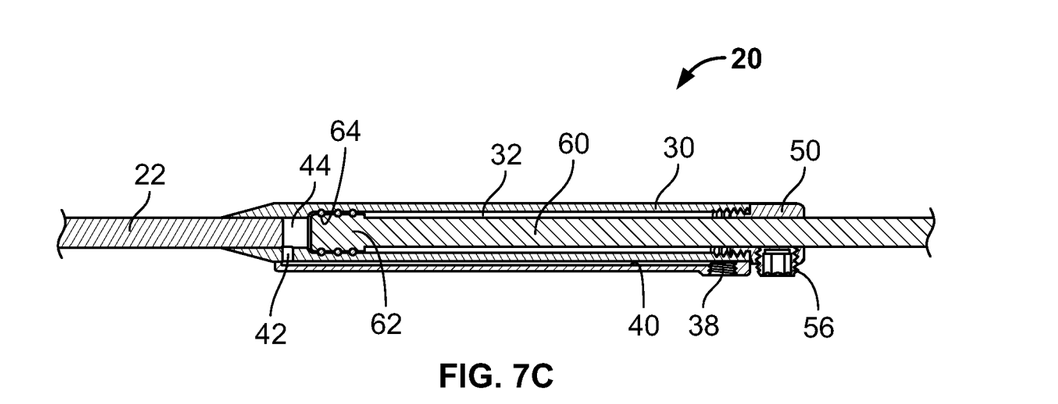
Figure 7D:
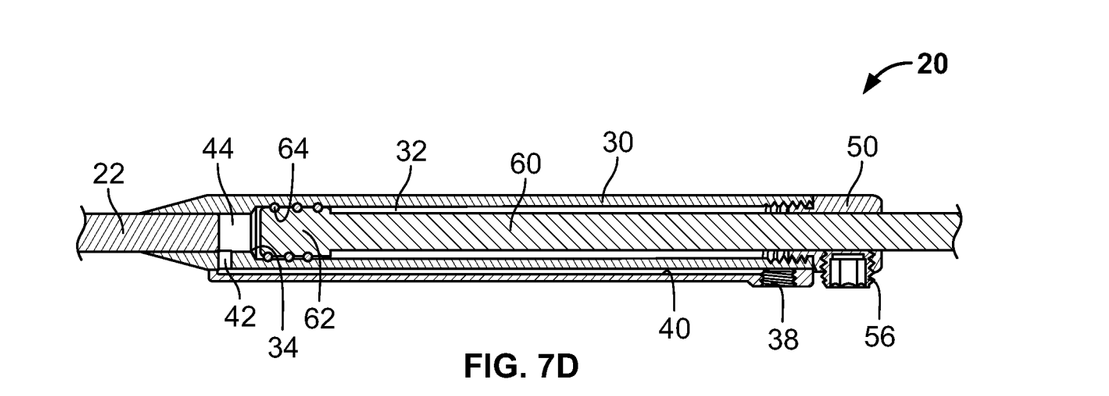
FIG. 7D is a close-up view of FIG. 7C.

An embodiment of an assembled hydraulic spinal rod 20 is shown in FIGS. 7A-D. As illustrated, internal cavity 32 of hydraulic cylinder 30 receives and allows movement of end portion 62 of piston rod 60 within cavity 32. With end portion 62 of piston rod 60 in internal cavity 32, capture nut 50 may be screwed into threaded end 36 of hydraulic cylinder 30 to permit movement of piston rod 62 in internal cavity 32 between stop 34 and projecting part 58 of capture nut 50. As capture nut 50 is secured to threaded end 36, piston rod 60 is rotatably secure relative to capture nut 50, static rod 22, and hydraulic cylinder 30 (e.g., due to the "keyed" nature of piston rod 60 and channel 52). In other words, the irregular shapes of piston rod 60 and channel 52 of capture nut 50 precludes or at least substantially inhibits relative rotational movement between piston rod 60 and capture nut 50. Piston rod 60 is therefore capable of moving axially within internal cavity 32 of hydraulic cylinder 30 to multiple different positions, without unwanted rotation, thereby allowing expansion of spinal rod 20 to different lengths. Seals 66 on end portion 62 of piston rod 60 may also sealingly close off portions of internal cavity 32 to the right and left of end portion 62, as shown in FIGS. 7C-D, and allow end portion 62 and piston rod 60 to move smoothly (without substantial friction) in internal cavity 32. In one embodiment, spinal rod 20 may be effectively lengthened by about at least one-hundred millimeters (100 mm) in successive intervals, as determined by the surgeon (e.g., successive ten millimeter (10 mm) lengthening procedures). In another embodiment, the spinal rod 20 may be lengthened by about anywhere between forty millimeters (40 mm) to two-hundred millimeters (200 mm) in successive intervals, as determined by the surgeon. After a lengthening procedure, set screw 56 can be used to lock spinal rod 20 in its expanded position (e.g., it may bear upon piston rod 60 to lock it relative to static rod 22).

In use, a surgeon first makes an incision into a patient's back and then implants one or more spinal rods 20 on the patient's spinal column 10 (e.g., via attachment of static and piston rods 22, 60 with pedicle screws 12). Static and piston rods 22, 60 may reside in the tulip portion of pedicle screws 12 and be affixed with a set screw or other fixing device (e.g., a cam mechanism), as is common, to prevent relative movement between static and piston rods 22, 60 and pedicle screws 12. As shown in FIG. 2B, rods 22 may be contoured during surgery or at manufacturing to conform to the shape of the particular spinal column 10 at issue. In an embodiment, a patient-specific contoured rod 20 may be created by way of first computer imaging the patient's spinal column 10 and then manufacturing a rod 20 with a particular curvature to meet the patient's specific anatomy. Thus, rods 22 may fit the particular patient's needs. At initial implantation, each rod 20 may be pre-configured in length to fit the patient's spinal column 10, and its curvature, or the surgeon may utilize the hydraulic mechanisms present in each rod 22 to initially set rods 22's length. As an example, each rod 22 may be selected from a kit of rods 22 having different lengths so as to fit the particular patient's anatomy, or a rod 22 may be selected and then hydraulically actuated to achieve an initial proper fit for the patient.

In the latter scenario discussed above, the surgeon would utilize a syringe device 16 of the type shown in FIGS. 1A-B to expand hydraulic rod 20 to its initial fit. In an embodiment, syringe device 16 attaches to injection port 38 of hydraulic cylinder 30 so as to establish a secure connection therebetween (e.g., via threading on a distal end of syringe device 16 and the threading of injection port 38). Subsequently, the surgeon may force a hydraulic fluid, such as an incompressible, biocompatible fluid (e.g., preferably sterile water or saline fluid, but also other biocompatible fluids such as liquid antibiotics, blood, or oils) under pressure into injection port 38. The fluid may flow into injection port 38, through flow channel 40, into and through opening 42, and finally into hydraulic pressure chamber 44 where the fluid can exert a force against end portion 62 of piston rod 60. Due to seals 66 surrounding end portion 62, and the attachment of static rod 22 to hydraulic cylinder 30, a sealed hydraulic pressure chamber 44 is created therebetween. The force generated by the surgeon in using syringe 16 can therefore be translated through the hydraulic fluid and directly act on end portion 62 of piston rod 60.

In one example, syringe 16 may include a powered or manual pump mechanism for forcing hydraulic fluid under pressure into injection port 38, or syringe 16 may include other manual means for undertaking the same (e.g., a plunger and a rotating screw mechanism for advancing a plunger of syringe 16 under pressure). Thus, the surgeon is afforded either a powered or manual syringe 16 to force hydraulic fluid under pressure into hydraulic cylinder 30 (specifically hydraulic pressure chamber 44). The surgeon can consequently cause movement of piston rod 60 within internal cavity 32 of hydraulic cylinder 30 by a desired amount to cause expansion of spinal rod 20, in terms of its length.

Figure 10:
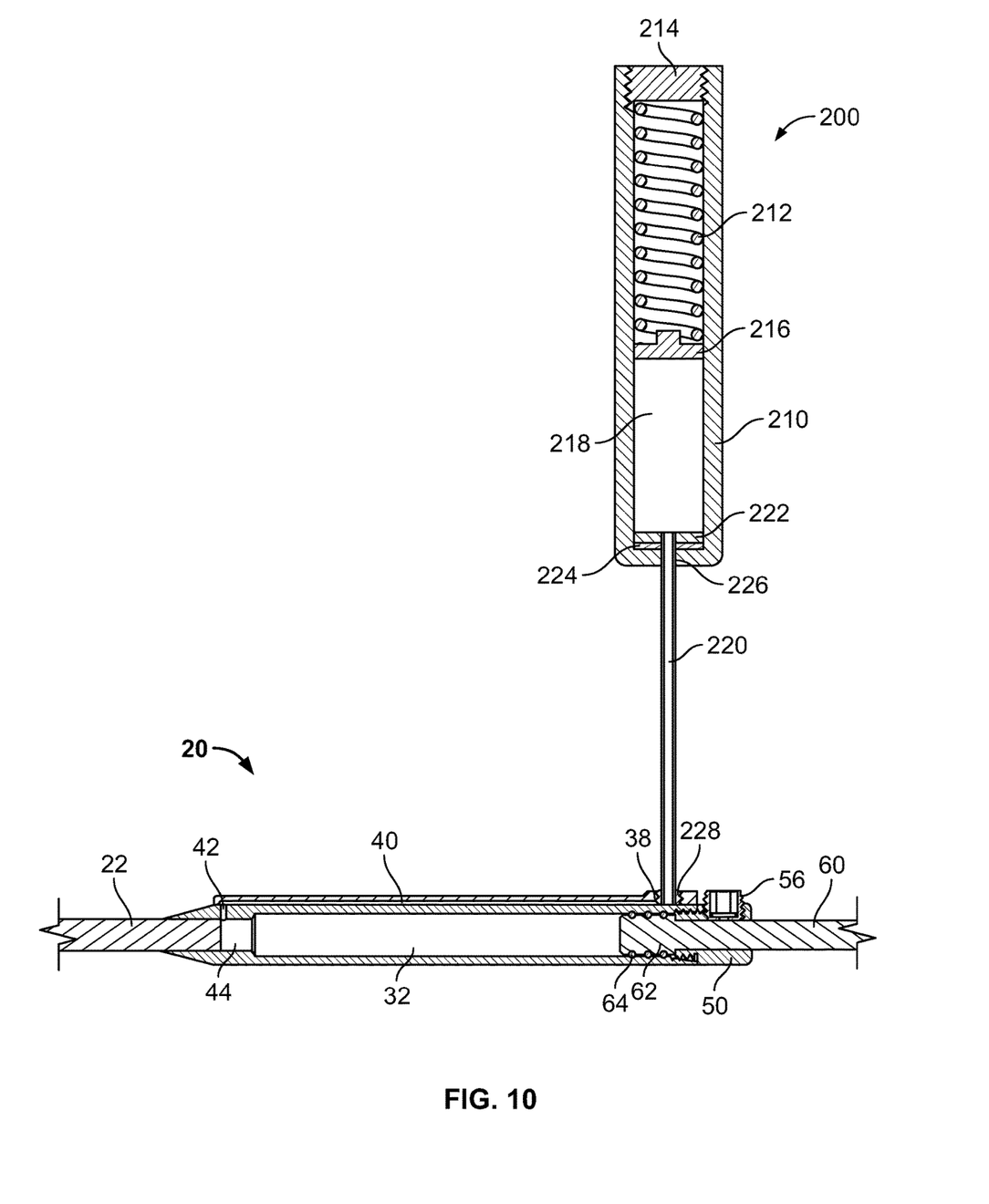
FIG. 10 is a cross-sectional view of the spinal rod of FIGS. 2A-B in which a pump is connected to the rod.

A specific embodiment illustrating a mechanical pump mechanism for expansion of spinal rod 20 is shown in FIG. 10. Although only rod 20 is shown in FIG. 10, it is equally contemplated that the pump mechanism described in connection with FIG. 10, or any other pump mechanism disclosed herein, could be used with rod 120 of FIGS. 8A-B (detailed below). As illustrated in FIG. 10, pump 200 is a mechanical pump that includes a hollow pump body 210, a spring 212 disposed in body 210, and a cap 214 and piston 216 surrounding spring 212. Pump body 210 includes a hollow bore 218 for containing an incompressible fluid of the type described above, and piston 216 sealingly contacts the walls of body 210 defining bore 218 so as to be able to drive the incompressible fluid out of pump 200. In this regard, cap 214 is, in an embodiment, threaded into pump body 210 and provides a stop for spring 212 at a first section of body 210, while piston 216 contacts spring 212 at a second section of body 210. Incompressible fluid is disposed beyond piston 216 within bore 218, and piston 216 acts on the fluid due to force generated by spring 212. In other words, spring 212 is compressed to some extent between piston 216 and cap 214 so as to force piston 216 in a downward direction within bore 218 against the incompressible fluid. In an embodiment, spring 212 is capable of exerting anywhere between about 0-1000 N of force on piston 216. As further shown in FIG. 10, pump body 210 is fluidly connected with a conduit 220, which extends through an opening 226 in pump body 210. Conduit 220 is attached (e.g., integral or monolithic) to a flange 222, which sits within bore 218 and is in turn in contact with a sealing member 224 disposed at a bottom part of pump body 210. The dimension/diameter of flange 222 is larger than that of opening 226 so that conduit 220 is securely retained in pump body 210. In addition, an end part of conduit 220 may also include a threaded nut 228 for engagement with injection port 38 of rod 20.

In use, pump 200 may cause incompressible fluid to expand spinal rod 20, much in the same way as described above (and below in connection with rod 120), through the action of spring 212 forcing piston 216 downwards against the incompressible fluid. Movement of piston 216 causes the incompressible fluid to travel through conduit 220 and into spinal rod 20 to expand rod 20 in the manner set forth above. Alternately stated, spring 212 is designed so that an appropriate amount of force is borne on piston 216 throughout rod 20's lifecycle, thereby generating enough distraction force between static and piston rods 22, 60 to cause the patient's spinal deformity (e.g., scoliotic curvature) to be corrected. As the patient grows, for example in the case of an adolescent patient, rod 20 with pump 200 attached can expand along with the patient's growth and exert a sufficient force on the patient's spinal column to cause correction of the deformity/curvature. As an example, rod 20 in use with pump 200 may be configured to initially exert a first distraction force of up to 1000 N on an adolescent patient's spinal column at implantation, decreasing progressively to a second distraction force of 0 N during rod 20's lifecycle. The first and second distraction forces mentioned above are, of course, sufficient to cause medically appropriate correction of the patient's deformity (e.g., straightening of the patient's spine). Spring 212 can also alternatively be designed to provide a constant distraction force for spinal rod 20 over time.

It should be noted that, although a mechanical pump has been described above, it is equally contemplated that an electrical pump, osmotic pump, or other type of low flow rate static pump could be used. In each of the aforementioned cases, the pump may also be implanted sub-dermally in the patient and, where applicable, actuated via an external actuation device. As an example, an induction, magnetic, or other internal motor could be used with the pump, which is actuated via an external actuation device to cause actuation of the pump and spinal rod 20's expansion. Using an electric pump as an illustrative case, the pump may have an internal electric motor that is capable of being actuated through induction or through other wireless means (e.g., a receiver). The system may also include an external controller for actuating the induction motor or other wireless mechanism causing the electric pump/motor to function. In an example, an RF transmitter or other like device could be incorporated into the controller for communicating with the above-mentioned wireless means.

To determine the appropriate amount of expansion, common medical imaging techniques (e.g., MRI, fluoroscopy, etc.) can be used to view spinal rod 20 after it has been expanded by some amount. Alternatively, a certain amount of force and pressure can be correlated to a particular lengthening for spinal rod 20. If rod 20 is expanded by an appropriate amount (a 10 mm expansion is common), the surgeon can then lock piston rod 60 via set screw 56 and fix the length of rod 20. In particular, a screw driver 14 of the type shown in FIGS. 1A-B may be used to rotate set screw 56 and cause it to bear against piston rod 60 to fix the overall length of rod 20. With rod 20 in position, the surgeon can then complete the surgery and close any incisions therefor. Of course, as noted above, the surgeon may alternatively be provided with a rod 20 that does not require alteration at initial implantation and only requires length expansion during subsequent surgical interventions. In one case, to finish expansion of spinal rod 20, the surgeon evacuates all, substantially all, or simply a majority of hydraulic fluid from hydraulic pressure chamber 44 and rod 20 after locking. As rod 20 is locked via set screw 56, it is not necessary to keep constant hydraulic pressure to maintain the positioning of static and piston rods 22, 60. In such an embodiment, a threaded plug (not shown) may be used to fluidly seal off injection port 38 after all or the necessary amount of hydraulic fluid is evacuated from rod 20.

After initial implantation, of either a lengthened or non-lengthened rod 20, the surgeon is afforded an opportunity to periodically lengthen hydraulic rod 20 using the same process described above. Thus, hydraulic fluid can be inserted into injection port 38 to cause expansion of rod 20 and correction of the underlying spinal deformity (e.g., scoliosis). In these expansion procedures, rod 20 may be unlocked at some point to allow for expansion, and then the surgeon may re-lock rod 20 and optionally withdraw the necessary amount of (e.g., all) hydraulic fluid from the system to finish the procedure. Thus, a growing spinal column 10 can be accommodated via rod 20.

The aforementioned surgical interventions (lengthening procedures) are not as demanding as typical procedures since only a small incision needs to be made to access injection port 38 and cause expansion of spinal rod 20. In some cases, the incision may be anywhere from about three to about six millimeters (3-6 mm) in length, and most preferably about four to about five millimeters (4-5 mm). As such, a pediatric patient with a growing spine can return to the surgeon on a periodic basis (e.g., every six (6) months) to confirm spinal rod 20's effectiveness and, if necessary, obtain an adjustment/lengthening. In some cases, the lengthening may be by about ten millimeters (10 mm) at each surgical intervention. At the culmination of the lengthening procedures, a fusion procedure may take place (if indicated) to ensure the patient's spinal column 10 remains in the corrected position. Thus, rod 20 presents an effective way to allow for expansion via non-invasive, periodic surgical interventions. In addition, in cases where a pump is implanted sub-dermally, surgical interventions for rod expansion post initial implantation are not necessary as rod 20 (or 120) expands on its own (e.g., via spring 212 when using pump 200), or through the use of an external actuation device, without surgical intervention.

Figure 9:
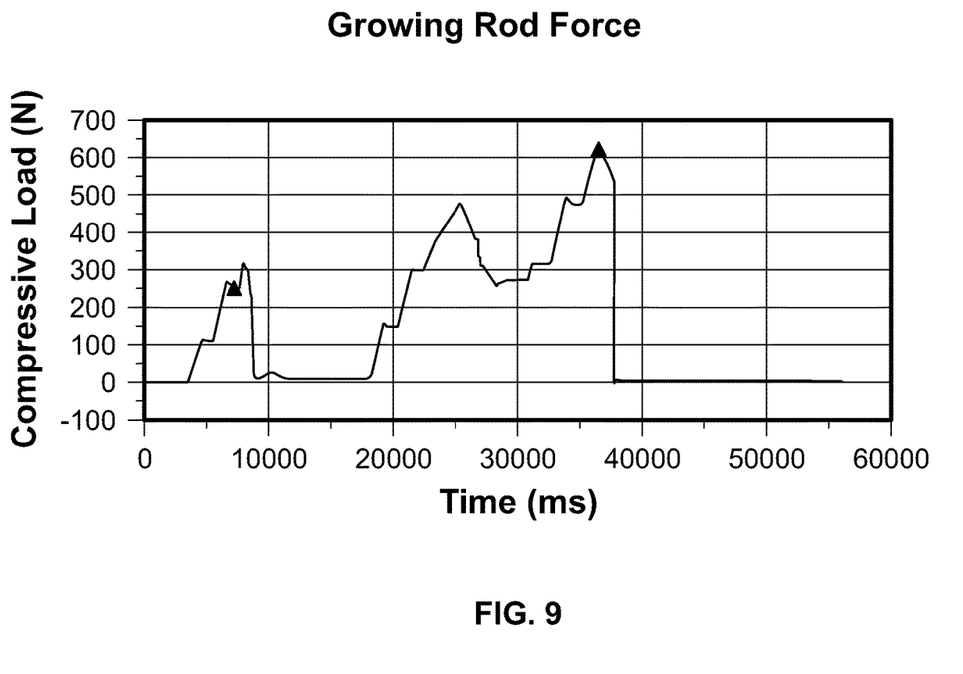
FIG. 9 is a chart demonstrating the results from testing the spinal rods of FIGS. 2A-B.

FIG. 9 shows a graph representing results obtained from testing an embodiment of a spinal rod 20, as described above. The graph demonstrates that peak forces of six hundred Newton's (600 N) were observed upon hydraulically expanding spinal rod 20, as well as lower forces. Thus, spinal rod 20 is capable of exerting forces of up to six hundred Newton's (600 N) or more on a patient's spinal column to correct the curvature thereof. Clinically, the amount of force required to expand a spinal rod, in situ, increases with each surgical intervention. Peak forces needed at, for example, the tenth lengthening procedure might be on the order of six hundred Newton's (600 N), while the first and third lengthening procedures might be one-hundred and forty (140 N) and one-hundred and sixty five (165 N) Newton's, respectively. Other existing expandable spinal rods have difficultly achieving the peak forces required for later-stage lengthening procedures, but due to the construction of the present spinal rod 20, peak forces needed for late-stage lengthening procedures can be achieved. The graph shown in FIG. 9 also does not represent failure testing for spinal rod 20, and rather it merely reflects testing to establish clinical efficacy. As such, rods 20 may exert even greater loads than those exemplified in FIG. 9 and still be within normal operating parameters. As an example, greater loading of rod 20 is possible using the pump mechanism of FIG. 10, as detailed above.

An additional benefit of rod 20 is the minimal or no surgical intervention that is required at each lengthening procedure. If surgical intervention is required, the minimally-invasive nature thereof is due in part to the closeness of injection port 38 and set-screw opening 54, in terms of proximity/location. Indeed, in one embodiment injection port 38 and set-screw opening 54 are spaced apart by about eight millimeters (8 mm). In another case, the distance may be anywhere from about five millimeters to about nine millimeters (5-9 mm). This small separation allows only a minimal incision to be made in the patient (e.g., of the size mentioned above) to gain access to both components of spinal rod 20 needed for expansion. In other words, as reflected by the closeness of screw driver 14 and syringe 16 in FIGS. 1A-B, only a small incision is needed to access the components necessary to expand rod 20 (i.e., injection port 38 and set screw 56). Thus, only a small incision is needed to affect expansion of rod 20, leading to only minor surgical trauma/side effects for the patient. In the case of using a pump mechanism, typically no surgical intervention is required. An additional benefit to rod 20 is that the patient will have increased thoracic growth because of the constant distraction pressure versus repetitive distractions performed at separate surgeries.

In an alternate embodiment, it is also possible to construct rod 20 so that injection port 38 and opening 54 are co-axial (e.g., they are the same opening) to experience possible greater benefits. For instance, capture nut 50 may not include opening 54 and instead injection port 38 may serve as a set-screw opening in addition to an injection port opening. In this case, injection port 38 would communicate directly with internal cavity 32 so that set screw 56 could be screwed into injection port 38 and bear on piston rod 60. Further, set screw 56 could itself include an opening that, when aligned appropriately with flow channel 40, would create a fluid flow channel through set screw 56 (in particular through its opening), into flow channel 40, through opening 42, and into hydraulic pressure chamber 44. In such a modification, internal cavity 32 could be sealed off from fluid interaction during an expansion procedure, for example because the end of set screw 56 is closed and fluid flow would only be possible through the opening in set screw 56 and into flow channel 40. Also, in such an embodiment the driver-engaging portion of set screw 56 may include threads for interacting with, for example, distal end of syringe 16. In this case, syringe 16 and screw driver 14 may be made into a combination instrument. In any case, the benefits of the close proximity between injection port 38 and set-screw opening 54 are apparent, as are the benefits resulting from an embodiment in which only a single opening is provided, as discussed above. Namely, only a small incision is needed to access such components and cause expansion of rod 20. Thus, the patient experiences less trauma and/or negative side effects.

Figure 8A:
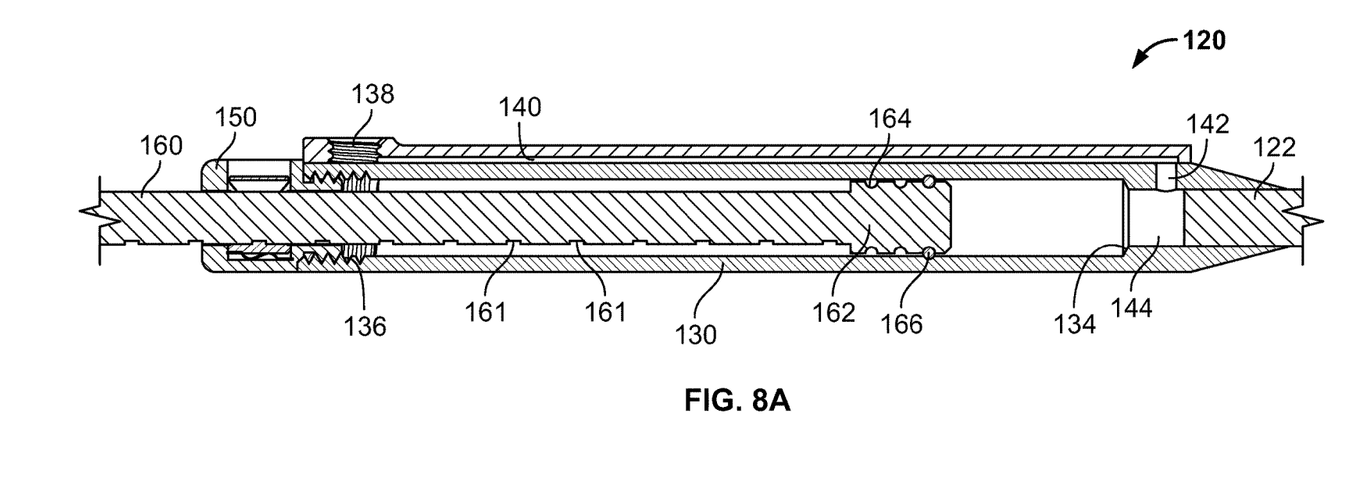
FIG. 8A is a cross-sectional view of an alternate embodiment of a spinal rod according to the present invention.
Figure 8B:
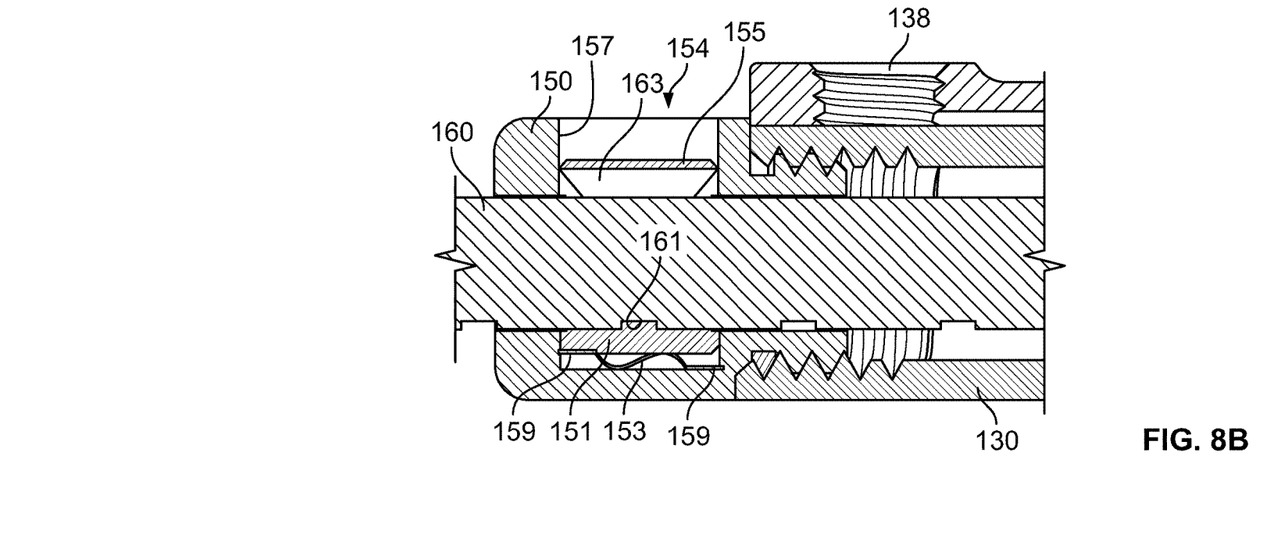
FIG. 8B is a close-up cross-sectional view of a portion of the spinal rod of FIG. 8A.

An alternate embodiment of a spinal rod 120 is shown in FIGS. 8A-B. Like numerals refer to like elements in this embodiment, but with numbers in the 100 series, and only the differences between spinal rods 20, 120 will be discussed.

Spinal rod 120 includes a different lengthening/locking structure as compared to spinal rod 20. In particular, as shown in FIG. 8A and in close-up in FIG. 8B, a ratcheting mechanism is used to achieve lengthening and locking of piston rod 160. In one embodiment, the ratcheting mechanism includes a capture nut 150, which has an opening 154 leading to an internal cavity 157. Inside of internal cavity 157 is a pawl 151 having one or more teeth that are sized to interact with teeth 161 formed on piston rod 160. Pawl 151 rests on a spring 153 disposed at a bottom end of internal cavity 157, which biases pawl 151 in the direction of opening 154. In an embodiment, spring 153 includes a set of legs 159 that rest, respectively, on a surface of pawl 151 and a floor defining internal cavity 157. In between legs 159 is a curvilinear segment forming the remainder of spring 153. As pawl 151 acts on legs 159 and the remainder of spring 153, spring 153 is caused to flex and allow for movement of pawl 151. As such, piston rod 160 can move in one direction due to movement of pawl 151 against spring 153 and out of engagement with teeth 161. As an example, pawl 151 can flex against spring 153 and allow movement of piston rod 160 in an expansion direction (left in FIGS. 8A-B), but not a contraction direction (right in FIGS. 8A-B). Thus, as rod 120 is hydraulically expanded (e.g., in the manner discussed above with respect to rod 20), pawl 151 can engage successive teeth 161 on piston rod 160 and ensure that piston rod 160 is locked relative to hydraulic cylinder 130 and static rod 122. In this embodiment, a set screw mechanism is therefore not needed.

If, for some reason, piston rod 160 is elongated too far, rod 120 also includes a release mechanism 155 for allowing movement of piston rod 160 in the contraction direction.

Release mechanism 155 may constitute an integral or unitary part of pawl 151 (e.g., a top portion or button thereof). Indeed, pawl 151 may be a tubular or cylindrical structure with a passageway 163 for accommodating piston rod 160, which is slightly larger in diameter/dimension than a diameter/dimension of piston rod 160. As such, release mechanism 155 of pawl 151 may be depressed by a user against the action of spring 153 to disengage the tooth or teeth of pawl 151 from the teeth 161 of piston rod 160. This would allow piston rod 160 to move in the contraction direction, as needed. For example, a user may utilize a tool to depress release mechanism 155 and consequently allow disengagement of pawl 151 from teeth 161 to permit movement of piston rod 160 in the contraction direction. Thus, if needed (e.g., if rod 120 is lengthened by too great an amount), release mechanism 155 may be used and the length of rod 120 may be shortened. While not mentioned above, it is to be appreciated that this type of contraction/shortening is also possible with set screw 56. As noted above in connection with the various pump mechanisms, rod 120 is also usable with any pump mechanism disclosed herein, including any sub-dermal pump, for expansion of rod 120 (e.g., to maintain a constant or variable distraction force for rod 120).

Figures 11A, 11B:
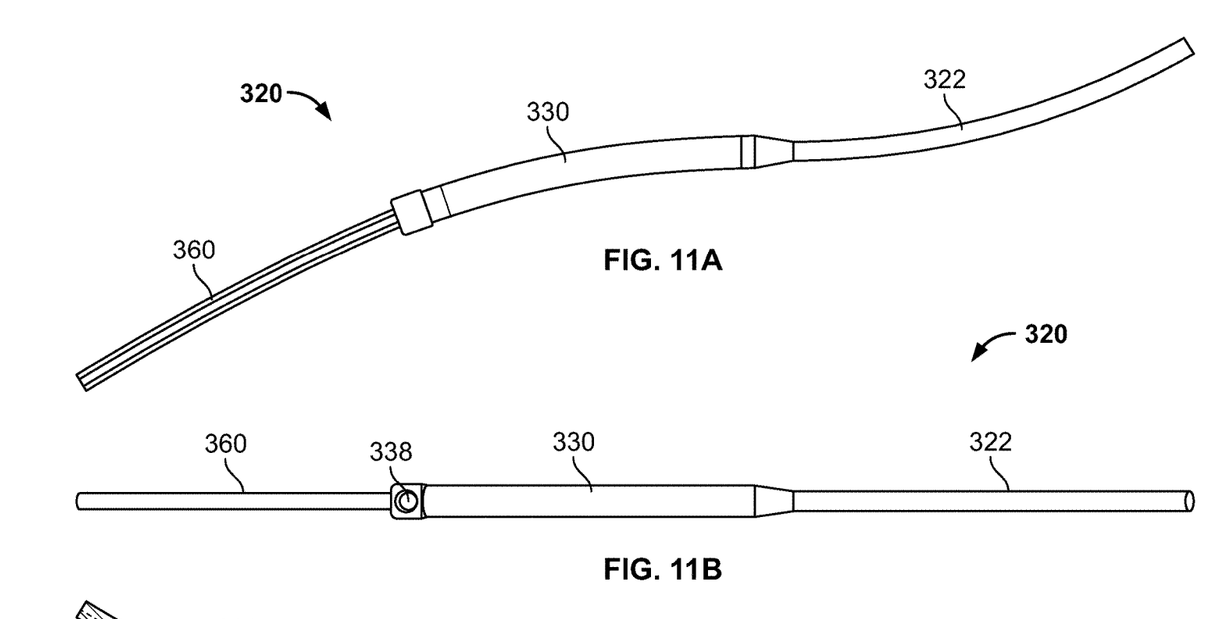
FIG. 11A is a side view of an alternate embodiment of a spinal rod according to the present invention.
FIG. 11B is a top view of the spinal rod of FIG. 11A.
Figure 11C:
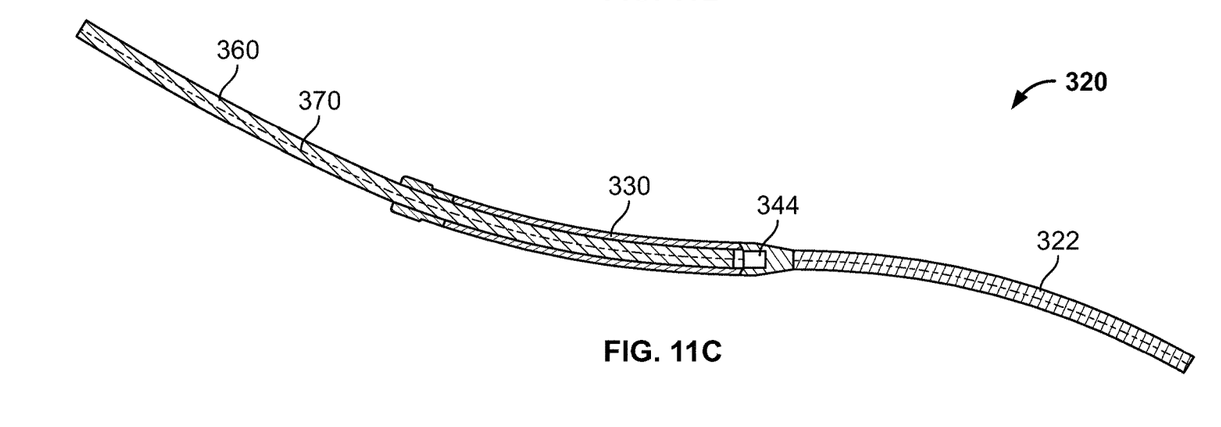
FIG. 11C is a cross-sectional side view of the spinal rod of FIG. 11A taken along the axis represented by the dotted line in FIG. 11B.

Yet another alternate embodiment of spinal rods 20, 120 is shown in FIGS. 11A-C. Like numerals refer to like elements in this embodiment, but with numbers in the 300 series, and only the differences between spinal rods 20, 120 and 320 will be discussed.

Although rod 320 is shown as being more closely aligned with the structure of rod 20 than rod 120, in that no ratchet mechanism is used, it should be recognized that the following discussion concerning rod 320 is equally applicable to rod 120 in the context of rod 120's ratchet mechanism. Put simply, the concepts and different structures of rod 320 can be utilized with rod 120 and its ratchet mechanism as well.

Rod 320 includes the same structures (e.g., internal cavity 32, flow channel 40, capture nut 50, seals 66, etc.) as rod 20, although a number of those structures are not designated by reference numerals in FIGS. 11A-C. For simplicity's sake, only the distinctions between rod 20 and rod 320 are highlighted. Rod 320 is different from rod 20 in that rod 320 has a curved shape along its length, including a curvature for hydraulic cylinder 330. Such curvature produces, for example, a curved internal cavity and a curved flow channel (both not designated by a reference numeral) extending to hydraulic pressure chamber 344. In particular, the internal cavity of hydraulic cylinder 330 is curved along its length due to the curvature of hydraulic cylinder 330, and the flow channel leading to hydraulic pressure chamber 344 is likewise curved.

In an embodiment, piston rod 360 of rod 320 is curved upwards for fixation to the lumbar spine exhibiting a lordotic curvature, hydraulic cylinder 330 is curved upwards and transitions to less of an upward curve as it approaches static rod 322 (e.g., hydraulic cylinder 330 has a variable curvature), and static rod 322 is curved downwards for fixation to the thoracic spine exhibiting a kyphotic curvature. In the end, the curvature of piston rod 360, hydraulic cylinder 330, and static rod 322 may follow an axis 370 that forms a substantially S-shaped curve. In an alternate embodiment, hydraulic cylinder 330 may transition from less of an upward curve to a downward curve as it approaches piston rod 322. Of course, as recognized above, the curved nature of rod 320 may be utilized in connection with rod 120 and its ratchet structure, although not described in detail herein.

In the devices shown in the figures, particular structures are shown as being adapted for use in the implantation, distraction, and/or removal of hydraulically-expandable spinal rods according to the present invention(s). The invention(s) also contemplates the use of any alternative structures for such purposes, including structures having different lengths, shapes, and/or configurations. For instance, although the disclosure references threaded structures in many cases (e.g., threaded end 36, 136 of hydraulic cylinder 30, 130, threaded injection port 38, 138, etc.), it is equally contemplated that non-threaded alternative engagement structures can be used. In particular, press-fit, bayoneted engagement structures, and/or ball-and-detent engagement structures may be used. In short, provided engagement between the referenced structures is achieved, any connecting structures can be used.

Further, while the hydraulic mechanism herein is described as a hydraulic cylinder 30, 130 it is not necessarily tied to that shape and any suitable shape can be used (e.g., square, rectangular, triangular, hexagonal, etc.) The same is true for hydraulic cylinder 30, 130's internal cavity 32, 132 and other components (e.g., end portion 62, 162 of piston rod 60, 160 fitting within such cavity 32, 132).

In addition, it is contemplated that while the rods 20, 120 herein are described as being formed from multiple components, such rods 20, 120 may instead be 3D printed to provide for less components and more unitary structures. For example, static rod 22, 122 and hydraulic cylinder 30, 130 may be 3D printed as a single component, along with injection port 38, 138 and flow channel 40, 140 (which are welded to hydraulic cylinder 30, 130 in the main embodiment).

As yet another example, while certain steps of the above-described method(s) are discussed in a particular order, it is to be understood that the order may be altered in any manner suitable to implant or distract the rods 20, 120 described above. Thus, the order of steps for the method(s) is not essential, and such order may be varied or changed in any manner considered suitable by one of skill in the art.

Although the invention(s) herein has been described with reference to particular embodiments, it is to be understood that these embodiments are merely illustrative of the principles and applications of the present invention(s). It is therefore to be understood that numerous modifications may be made to the illustrative embodiments and that other arrangements may be devised without departing from the spirit and scope of the present invention(s) as defined by the appended claims.

It will also be appreciated that the various dependent claims and the features set forth therein can be combined in different ways than presented in the initial claims, and that the features described in connection with individual embodiments may be shared with others of the described embodiments. In particular, as understood by one of skill in the art, the features of any dependent claim may be shared with a separate independent or dependent claim, to the extent feasible.

The invention claimed is:

1. An expandable spinal rod system comprising:
a first rod portion having an internal cavity;
a second rod portion at least partially positioned within the internal cavity of the first rod portion, and moveable in a first direction relative to the first rod portion, the second rod portion having an elongate rod section having a longitudinal length with a constant cross-sectional shape, the cross-section being transverse to the longitudinal length, wherein the second rod portion sealingly engages an internal wall surface of the internal cavity thereby defining a hydraulic pressure chamber;
a locking member engageable with a tapered surface of the first rod portion and that bears on the elongate rod section of the second rod portion to prevent the second rod portion from moving in a second direction opposite the first direction; and
a pump configured for implantation sub-dermally in a patient, the pump being fluidly connected with the hydraulic pressure chamber.

2. The spinal rod system of claim 1, wherein the locking member is moveable in a first locking direction.

3. The spinal rod system of claim 2, wherein the locking member is moveable in a second releasing direction, opposite the first locking direction.

4. The spinal rod system of claim 3, wherein at least one of or both of the first locking direction and the second releasing direction extend along an axis that intersects a longitudinal axis of the second rod portion.

5. The spinal rod system of claim 1, further comprising an injection port in fluid communication with the hydraulic pressure chamber.

6. The spinal rod system of claim 1, wherein the pump is an osmotic pump.

7. The spinal rod system of claim 1, wherein movement of the second rod portion relative to the first rod portion within the internal cavity alters the size of the hydraulic pressure chamber.

8. The spinal rod system of claim 1, wherein the first and second rod portions are curved.

9. The spinal rod system of claim 1, wherein the first portion has an elongate rod section adapted for connection with a first fixation element implanted in a first vertebra.

10. The spinal rod system of claim 1, wherein the first direction is an expansion direction and the second direction is a contraction direction.

11. A hydraulically expandable spinal rod system comprising:
a first rod portion having an internal cavity;
a second rod portion having a longitudinal axis and being at least partially positioned within the internal cavity of the first rod portion, and moveable in a first direction relative to the first rod portion, the second rod portion having an elongate rod section having a longitudinal length with a constant cross-sectional shape, the cross-section being transverse to the longitudinal length; and
a locking member moveable along an axis that intersects the longitudinal axis of the second rod portion and that bears on the elongate rod section of the second rod portion prevent the second rod portion from moving in a second direction, opposite the first direction,
wherein the second rod portion sealingly engages an internal wall surface of the internal cavity thereby defining a hydraulic pressure chamber for receiving hydraulic material, the hydraulic material causing the second rod portion to move in the first direction.

12. An expandable spinal rod system comprising:
a first rod portion having an internal cavity and a hydraulic pressure chamber;
a second rod portion at least partially positioned within the internal cavity of the first rod portion, and moveable in a first direction relative to the first rod portion, the second rod portion having an elongate rod section having a longitudinal length with a constant cross-sectional shape, the cross-section being transverse to the longitudinal length; and
a locking member engageable with a tapered surface of the first rod portion and that bears on the elongate rod section of the second rod portion to prevent the second rod portion from moving in a second direction opposite the first direction; and
an osmotic pump in fluid communication with the hydraulic pressure chamber and being configured to cause the second rod portion to move in the first direction.

13. The spinal rod system of claim 12, wherein the locking member is moveable along an axis that intersects with a longitudinal axis of the second rod portion.

14. An expandable spinal rod system comprising:
a first rod portion having an internal cavity;
a second rod portion at least partially positioned within the internal cavity of the first rod portion, and moveable in a first direction relative to the first rod portion, the second rod portion having an elongate rod section having a longitudinal length with a constant cross-sectional shape, the cross-section being transverse to the longitudinal length, wherein the second rod portion sealingly engages an internal wall surface of the internal cavity thereby defining a hydraulic pressure chamber;
a locking member engageable with a tapered surface of the first rod portion and that bears on the elongate rod section of the second rod portion to prevent the second rod portion from moving in a second direction opposite the first direction; and
an injection port in fluid communication with the hydraulic pressure chamber.

* * * * *